US006879741B2

(12) United States Patent
Salerno et al.

(10) Patent No.: US 6,879,741 B2
(45) Date of Patent: Apr. 12, 2005

(54) SAMPLING END FOR FIBER OPTIC PROBE (75) Inventors: Mark Salerno, Cranford, NJ (US);
Craig D. Harrison, Cedar Knolls, NJ (US); Ishai Nir, Hamilton, NJ (US);
Hans DeWaal, Newfoundland, NJ (US); Mario Vieira, Caldwell, NJ (US)

(73) Assignee: C Technologies, Inc, Cedar Knolls, NJ (US)

( * ) Notice: Subject to any disclaimer, the term of this patent is extended or adjusted under 35 U.S.C. 154(b) by 112 days.

(21) Appl. No.: 10/287,114

(22) Filed: Nov. 4, 2002

(65) Prior Publication Data

US 2004/0086215 A1 May 6, 2004

(51) Int. Cl.$^7$ .................................................. G02B 6/00
(52) U.S. Cl. ......................... 385/12; 385/117; 356/301
(58) Field of Search .................... 385/12, 13, 115–121; 356/301, 402, 436; 250/458.1, 574; 600/344, 476

(56) References Cited

U.S. PATENT DOCUMENTS

| | | | |
|---|---|---|---|
| 2,987,960 A | 6/1961 | Sheldon | 88/72 |
| 3,434,775 A | 3/1969 | Gosselin | 350/96 |
| 3,494,354 A | 2/1970 | Yokota et al. | 128/6 |
| 3,548,808 A | 12/1970 | Takahashi et al. | 128/6 |
| 3,945,371 A | 3/1976 | Adelman | 128/2 |
| 4,281,929 A | 8/1981 | Lord et al. | 356/241 |
| 4,727,859 A | 3/1988 | Lia | 128/6 |
| 4,820,015 A | 4/1989 | Mogi | 350/96.24 |
| 4,909,588 A | 3/1990 | Harner et al. | 350/96.2 |
| 4,917,491 A | 4/1990 | Ring et al. | 356/300 |
| 4,974,929 A | 12/1990 | Curry | 350/96.29 |
| 5,044,755 A | 9/1991 | Landa et al. | 356/440 |
| 5,107,847 A | 4/1992 | Knute et al. | 128/675 |
| 5,134,280 A | 7/1992 | Johnston et al. | 250/227.11 |
| 5,241,368 A | 8/1993 | Ponstingl et al. | 356/436 |
| 5,327,880 A | 7/1994 | Harley et al. | 128/6 |
| 5,335,067 A | 8/1994 | Prather et al. | 356/436 |
| 5,418,615 A | 5/1995 | Doyle | 356/436 |
| 5,431,646 A | 7/1995 | Vassiliadis et al. | 606/6 |
| 5,510,895 A | 4/1996 | Sahagen | 356/436 |
| 5,526,112 A | 6/1996 | Sahagen | 356/72 |
| 5,557,099 A | 9/1996 | Zielinski et al. | 250/227.11 |
| 5,652,810 A * | 7/1997 | Tipton et al. | 385/12 |
| 5,704,892 A | 1/1998 | Adair | 600/121 |
| 5,743,731 A | 4/1998 | Lares et al. | 433/29 |
| 5,754,722 A | 5/1998 | Melling | 385/115 |
| 5,769,791 A | 6/1998 | Benaron et al. | 600/473 |
| 5,771,327 A | 6/1998 | Bar-Or et al. | 385/139 |
| 5,772,597 A | 6/1998 | Goldberger et al. | 600/473 |
| 5,833,683 A | 11/1998 | Fuller et al. | 606/17 |
| 5,841,545 A | 11/1998 | Young | 356/436 |
| 5,930,440 A | 7/1999 | Bar-Or | 385/136 |
| 6,052,184 A | 4/2000 | Reed | 356/338 |
| 6,095,974 A | 8/2000 | Shemwell et al. | 600/310 |
| 6,197,575 B1 | 3/2001 | Griffith et al. | 435/288.4 |
| 6,205,272 B1 | 3/2001 | O'Rourke et al. | 385/33 |
| 6,239,875 B1 | 5/2001 | Verheijen | 356/436 |
| 6,332,092 B1 | 12/2001 | Deckert et al. | 600/476 |
| 6,333,784 B1 | 12/2001 | Blasi et al. | 356/72 |
| 6,370,406 B1 | 4/2002 | Wach et al. | 300/310 |
| 2001/0035957 A1 | 11/2001 | Clermont et al. | |
| 2001/0055462 A1 | 12/2001 | Seibel | |
| 2002/0007111 A1 | 1/2002 | Deckert et al. | |

OTHER PUBLICATIONS

C Technologies, Inc., "Fiber Optic Probes: Bringing the Measurements to Your Sample," Jun., 2002. Ocean Optics, Inc., "pH Sensors & Accessories," 2001.

* cited by examiner

Primary Examiner—Phan T. H. Palmer
(74) Attorney, Agent, or Firm—Wolff & Samson (57) ABSTRACT

A fiber optic probe device having a sampling end positionable over optical fibers is provided. The sleeve could be releasably attached to the fiber optic probe device. The sampling end can be discarded after use, or re-used. A sample chamber including a reflective surface can be formed at the distal end of the sampling end.

79 Claims, 11 Drawing Sheets

SAMPLING END FOR FIBER OPTIC PROBE

BACKGROUND OF THE INVENTION

1. Field of the Invention

The present invention relates to a fiber optic probe device and more particularly to a fiber optic probe device having a sampling end positionable over the optical fibers.

2. Related Art

Fiber optic probes have long been used to measure the properties of solutions. Such probes use optical fibers to send out light to interact with the solution. The light is then picked up by the optical fibers. This received light includes information about the characteristics of the solution. Fiber optic probes can be used in various applications including manufacturing processes, medical applications, remote measurements in harsh environments, monitoring ground water flow, etc.

One type of fiber optic probe includes transmitting and receiving optical fibers that extend side by side down the probe. One of the fibers terminates while the other extends beyond the first fiber and then back up so that it is in a facing relation with the first fiber. There is a gap between the fibers. The device can be placed into a solution. The solution flows into the gap between the transmitting and receiving fibers. Light is transmitted through the gap where it interacts with the solution and is received by the receiving fiber. Data is obtained and processed to provide information about the solution. Other probes are configured such that light passes through the liquid and is reflected off a mirror back through the liquid where it is received.

Conventional fiber optic probes, however, have some drawbacks. One such drawback is the potential for contamination which can occur when a probe from one solution is not completely cleaned and then inserted into another solution. Part of the first solution can be inadvertently added to the second solution to contaminate the second solution. Accordingly, rigorous cleaning and sterilization procedures are required between measurements of first and second solutions.

Another problem associated with conventional fiber optic probes is that the components of the probe are often made separately and then attached together using epoxies and adhesives. For example, a probe housing made of metal having an optical window made of glass or other light transparent material requires an epoxy or adhesive to attach the optical window to the metal probe housing. Organic compounds such as epoxies and adhesives may react with solutions to contaminate samples and provide for inaccurate measurements. Additionally, the reactivity of organics such as epoxies and adhesives causes them to dissolve or become eaten away, which eventually damages the probe.

Accordingly, what is needed, but has not heretofore been provided, is a fiber optic probe having a sampling end that is of a unitary construction and does not require adhesives, epoxies or other organics for attachment of components. It would also be desirable to have a sampling end for a fiber optic probe that can be discarded after use, or cleaned and reused. Further, it would be desirable to have a sampling end for a fiber optic probe cover that is capable of easy attachment and detachment with a probe so that it can be attached, used, released and discarded. It would also be desirable to have the option for such operation to be automated so that it could be performed without the need for human intervention.

SUMMARY OF THE INVENTION

The present invention relates to a fiber optic probe device including a handle, optical fibers extending from the handle, and a sampling end positionable over the optical fibers. The sampling end may be in the form of an elongated tube having an open end and a closed end. The fiber optics extend from the handle into the sampling end through the open end to abut the closed end of the sampling end. The open end of the sampling end is preferably releasably attached to the handle or the optical fibers. The elongated tube is preferably circular in cross section, but could take on other shapes. An optical window is at the closed end of the tube. It could be formed as part of the tube, or could be attached thereto. The optical window allows for light to pass to and from the optical fibers within the elongated tube.

In one embodiment, a mirrored surface is spaced from and positioned to face the optical window of the elongated tube to reflect light traveling through a fluid medium from one optical fiber, or fibers, back through the fluid medium to the other optical fiber, or fibers. This arrangement can be constructed by attachment of a channel to the optical window of the elongated tube. The channel includes a bottom wall coated to be reflective, and two upstanding side walls attachable to the optical window of the elongated tube. Alternatively, the channel could have four sides, the upper wall forming the optical window. Either way, the fluid medium can pass between the optical window and the reflective bottom wall. This allows light to pass from one optical fiber, or fibers, through the optical window, through the fluid medium to the reflective bottom wall, where the light is reflected back through the fluid medium, and through the optical window to the other optical fiber, or fibers.

In another embodiment, the sampling end can be used without a reflective surface and the outer side of the optical window of the elongated tube can be coated with a chemical composition which may be reactive with a component of a fluid medium. Light from the optical fibers can pass back and forth through the optical window of the elongated tube. Any reaction caused by the chemical composition will influence the light returning to the optical fibers and provide data on the fluid medium.

The sampling end of the present invention is preferably releasably attached to the handle of the probe to allow for the sampling end to be attached, used, released and replaced. The sampling end could be discarded after use or it could be cleaned and re-used.

BRIEF DESCRIPTION OF THE DRAWINGS

Other important objects and features of the invention will be apparent from the following Detailed Description of the Invention taken in connection with the accompanying drawings in which.

DETAILED DESCRIPTION OF THE INVENTION

The present invention relates to a fiber optic probe device having a sampling end positionable over optical fibers. The sampling end may be attachable to a probe handle or to the optical fibers. The sampling end comprises an elongate tube having an open end and a closed end. The optical fibers extend from the handle, through the open end of the sampling end to abut the closed end of the sampling end. The open end of the sampling is preferably releasably attached to the handle, or the optical fibers. The sampling end can be attached, used, released and replaced. It can be discarded after use or re-used. The closed end comprises an optical window which allows for light to pass into and out of the optical fibers. A sample chamber can be positioned at the closed end of the sampling end. As will be discussed, in an alternative embodiment, the sampling end can be associated with a vessel, pipe or other fluid container and the optical fibers inserted thereinto for taking measurements.

Figure 1:
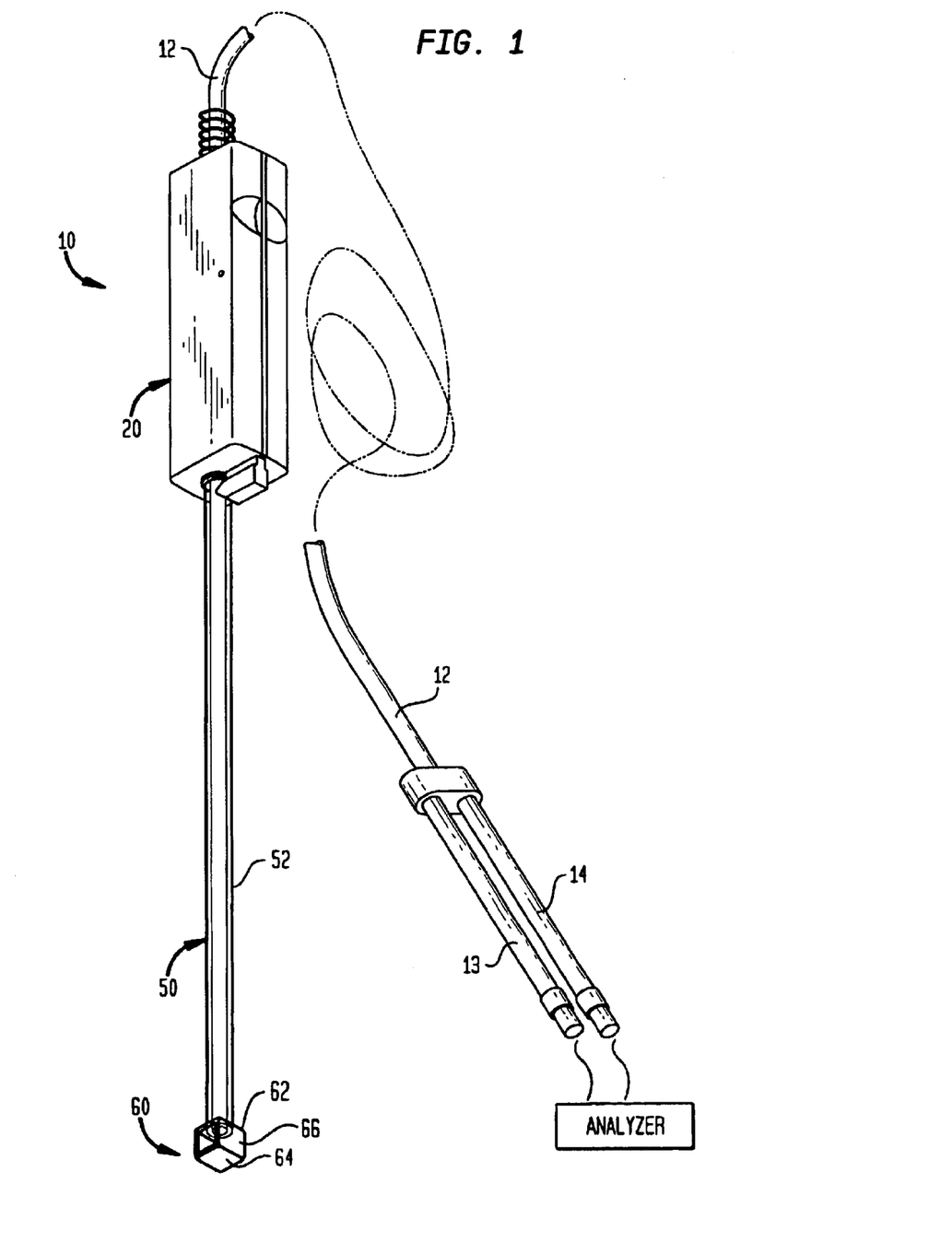
FIG. 1 is a perspective view of an embodiment of the fiber optic probe device of the present invention.

FIG. 1 is a perspective view of an embodiment of the fiber optic probe device, generally indicated at 10, of the present invention. A fiber optic lead 12 typically including a first fiber 13 and a second fiber 14, one of which being an input fiber and the other an output fiber, are fed from an analyzer into one end of the probe handle 20. The optical fibers extend through the probe handle 20 and out the other end where they are covered by sampling end 50. As shown in this embodiment, sampling end 50 comprises a cylinder 52. In this embodiment, the sampling end also comprises a sample chamber generally indicated at 60. While the cylinder 52 shown in the drawings has a round cross-section, it should be understood that the cross-section can be varied. The cylinder 52 has an open upper end and a closed distal end. An optical window (optically transparent to allow light to transmit therethrough) is provided at the distal end. The diameter of the cylinder can be varied as desired. For some applications, a certain sampling end size may be acceptable for beakers or cuvettes, while a much smaller size may be more appropriate for medical applications such as blood analysis. The length of the device can likewise be varied as desired. Indeed, a relatively long end could be used for testing at a remote location, for example, at the bottom of a well.

Figures 2A, 2B, 3:
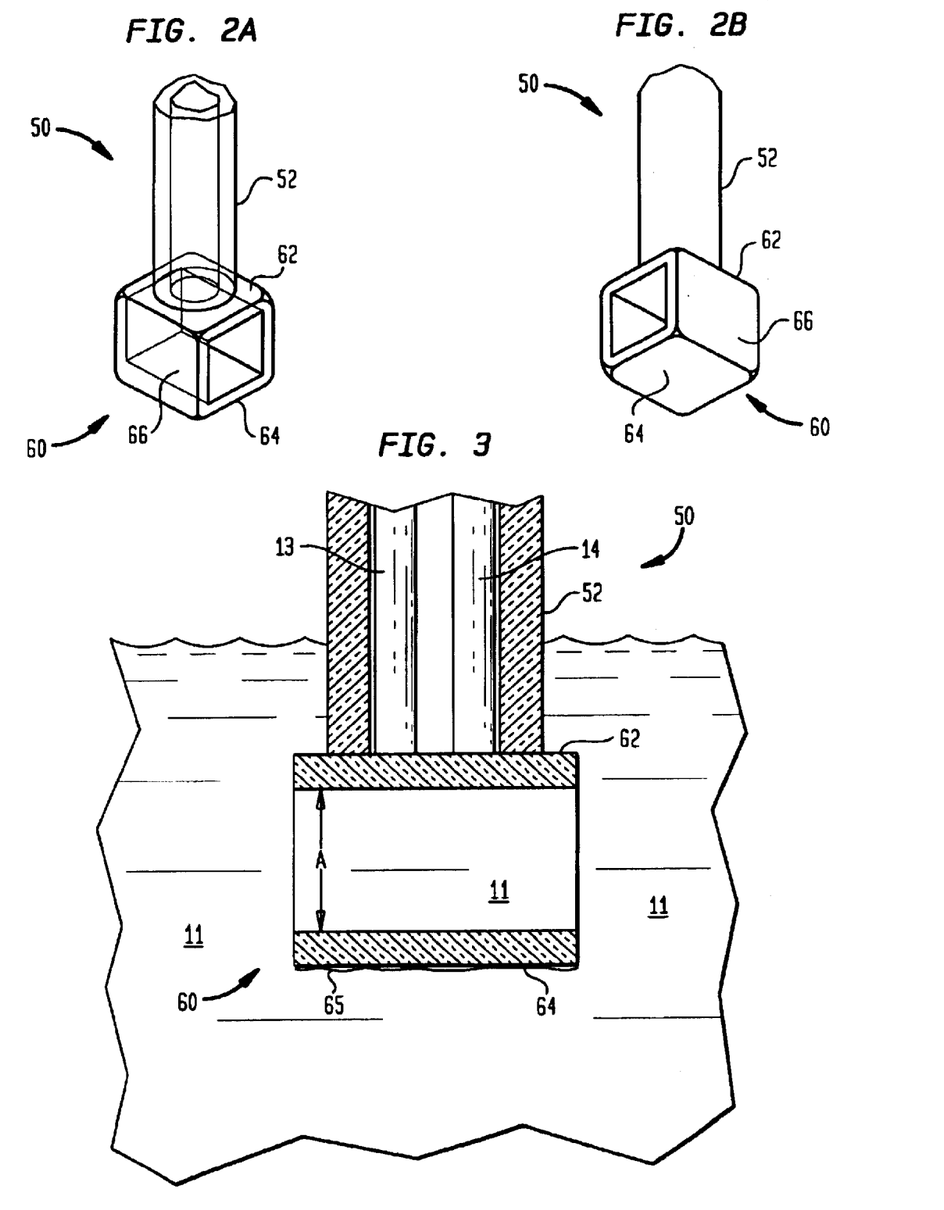
FIG. 2A is a partial perspective view of the end portion of the sampling end of the fiber optic probe shown in FIG. 1.
FIG. 2B is a partial perspective view showing the end portion of the sampling end shown in FIG. 2A from a different perspective.
FIG. 3 is a cross sectional view of the bottom portion of the sampling end shown in FIG. 1 immersed in a solution.

As shown in more detail in FIGS. 2A and 2B, the sample chamber 60 is defined by upper wall 62, bottom wall 64 and side walls 66. Bottom wall 64 is spaced apart from upper wall 62 and maintained in position by side walls 66. Thus, a chamber with open ends is formed. The optical window of the cylinder 52 can function as the upper wall, or more likely, the upper wall 62 can function as the optical window. The chamber 60 is preferably fused to cylinder 52 to eliminate the need for reactive epoxies or adhesives. However, for applications where reactivity is not a concern, the chamber 60 could be adhered or otherwise mechanically attached to cylinder 52.

Figure 7:
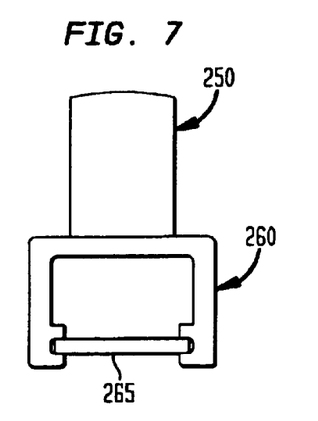
FIG. 7 shows a side view of another embodiment of a fiber optic probe device according to the present invention.

As shown in FIG. 3, the optical fibers 13 and 14 are positioned within the cylinder 52 of sampling end 50. Solution 11 can flow into sample chamber 60 between upper and bottom walls 62 and 64 for sampling. Importantly, it is desirable that the bottom wall 62 have a reflective surface 65 to reflect light from an output fiber in cylinder 52 back to an input fiber in cylinder 52. Such a reflective surface is preferably coated on the lower surface of bottom wall 64, but it could be coated on an upper surface thereof. Different coatings could be used depending on the application. Reflective coatings include, but are not limited to, aluminum and gold. Specialized coatings can be used to reflect only certain bands of light. Other coatings such as filters, diffusers, attenuators, etc., could also be used depending on the application. The coatings could be applied in any manner known in the art such as be deposition, dipping, electroplating, etc. It should also be noted that a mirror could be pressed or molded onto the bottom wall of the sample chamber during manufacturing. Also, as shown in FIG. 7, a mirror 265 can be inserted in a slot formed by protuberances at the distal end of sample chamber 260. Such a configuration could be used for an application where it is suitable to make the sample end 250 and chamber 260 of plastic.

One type of filter that can be used functions as a selection device that allows for exclusive measurement of an item of interest without interference from others. For example, in a fluorescence-type measurement, the sample is excited by light from the instrument and then analyzed for the presence of a specific item by coating the window of the sleeve with a filter that will only transmit at a wavelength corresponding to an emission indicative of the item to be measured. Another type of filter that can be employed is a solar blind filter to discriminate against room light. This filter only transmits UV from the instrument rather than light from the environment and allows for operation of the probe when the room lights are on. A physical filter or membrane can be attached to the openings of the sample chamber to permit only certain materials to pass into the measurement area to provide selectivity between materials that otherwise could not be discriminated. For example, the membrane can be permeable only to oxygen and could be used to keep other reactive components outside of the sample chamber.

Figure 8:
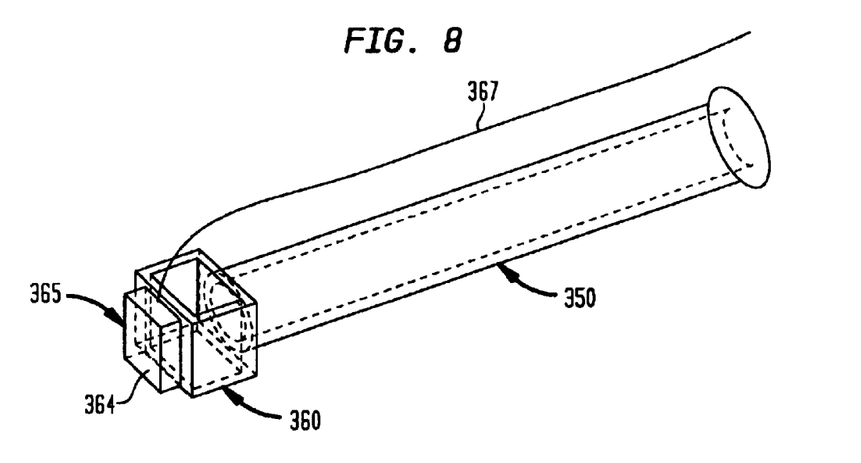
FIG. 8 is a perspective view of another embodiment of the fiber optic probe device shown in FIG. 1 having a detector at the bottom of the sample chamber.

It should also be pointed out that it may be desirable to include various optical components on the distal end of the sampling end. Such components could include, but are not limited to, prisms, mirrors, hemispheres, ATR crystals, etc. Further, as shown in FIG. 8, a detector or transducer 365 could be placed at the bottom wall 364 of chamber 360 of sampling end 350 to receive light. The detector could be attached to or buried in the bottom wall, and the electrical signal wired back through a lead 367, which could be deposited on or inside the sampling end, or an electrical conduit could be provided on or in the sampling end. Alternatively, a wire could run through a fused piece of capillary. Alternatively, the electrical conduit could be deposited in the sampling end. It would be desirable to include a mechanism for orienting the sampling end with the handle for providing electrical communication between the sampling end and the handle. This could be done by aligning marks on the handle and the sampling, or more preferably, by keying the sampling end so that it can only be attached to the handle when properly oriented. The presence of an electrical lead could also allow for the delivery of electrical energy to the sample point for possible use in analysis. Also, LED's could be positioned at the distal end of the sampling end. The LED's could be positioned in a chamber adjacent the sample zone to allow for 90 degree offset measurements of fluorescence. The inclusion of an electrical conduit could also allow for providing other sensors at the distal end of the sleeve, such as a temperature sensor.

Referring back to FIG. 3, it can be seen that there exists a distance between the upper wall 62 and the lower wall 64 of sample chamber 60 as indicated by letter A. This distance can be altered depending upon the solution being measured. Preferably, the gap A is equal to one half of the pathlength. Because light travels along distance A twice, the pathlength is twice the size of gap A. Different solution measurements require different pathlengths. For example, it may be desirable to have a small pathlength for an opaque solution, and a long pathlength for a solution with a low concentration of the substance for the testing is directed. Accordingly, sampling ends can be made with specific gaps A for specific measuring specific solutions.

Figure 4:
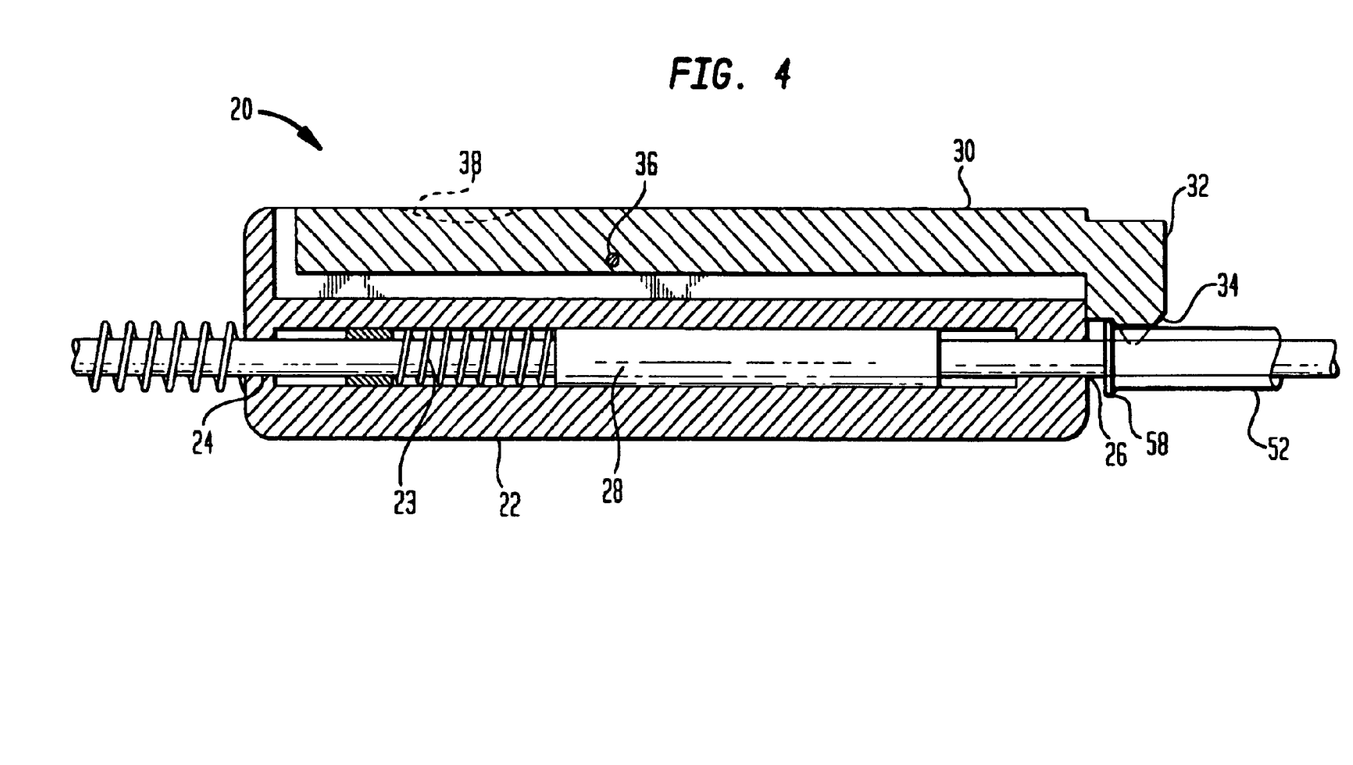
FIG. 4 is a cross-sectional view of the handle shown in FIG. 1.

FIG. 4 is a cross-section view of an embodiment of a handle, generally indicated at 20, for use with the fiber optic probe device of the present invention. As can be seen, the handle 20 comprises a housing 22 having an entry aperture 24 for interconnection with fiber optic input and output lines, and an exit aperture 26 for permitting optical fibers to extend from the housing 22. A passageway 28 extends through the housing.

It is preferable that the distal ends of the optical fibers contact the optical window of the sampling end. To facilitate such a configuration, it is desirable that the fiber optics be moveable with respect to the handle. Accordingly, bias means such as spring 23 can be used to allow the optical fibers extending from the handle to be retracted into the handle upon application of pressure against the distal end of the fibers such as may occur when the optical window of a sampling end bears against the distal ends of the optical fibers.

A locking lever 30 is interconnected with the handle 20 for locking and unlocking sleeve 50 to the handle 20. The locking lever 30 has a head 32 with a nose 34 which can extend over a ridge or a flared upper edge 58 of cylinder 52. The locking lever 30 is pivotally interconnected with the handle 20 at pivot point 36. Touch point 38 is provided at the far side of pivot 36. The touch point 38 can be depressed to pivot the head 32 and nose 34 in and out of contact with cylinder 52 to lock or unlock the cylinder 52 to the handle 20. Other configurations for the locking lever, as well as other configurations for attaching the cylinder to the handle, are considered within the scope of the present invention.

Figure 5A:
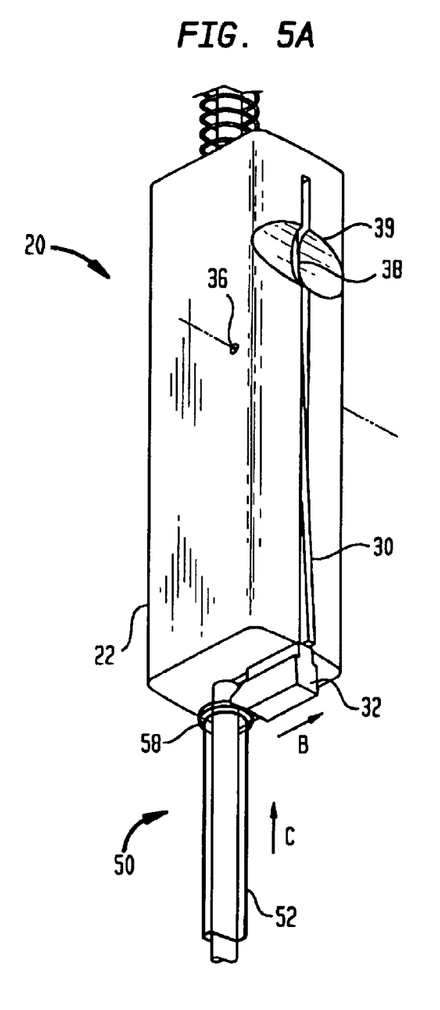
FIGS. 5A and 5B are perspective views showing actuation of the handle shown in FIG. 1 for attaching a sampling end thereto.
Figure 5B:
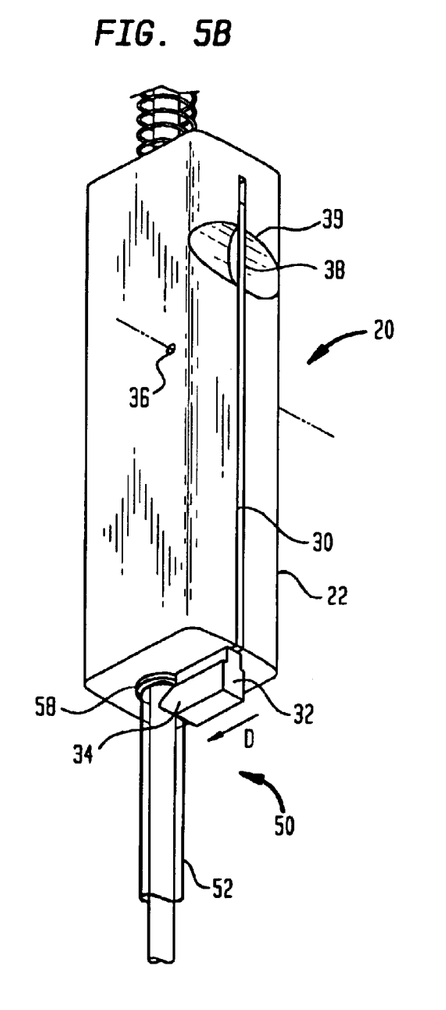

FIGS. 5a and 5b are perspective views showing the actuation of the handle 20. The handle 20 includes a recess 39 which allows the locking lever 30 to be actuated by applying pressure to touch point 38 which in turn moves head 32 and nose 34 away from cylinder 52 to allow cylinder 52 to be moved with respect to handle 20. As shown in FIG. 5a, the head 32 is moved in the direction of arrow B to allow the flared end 58 of cylinder 52 to be moved passed nose 34 in the direction of arrow C. Once the cylinder 52 is in place, pressure can be taken off of touch point 38 to allow the nose 34 to move into engagement with cylinder 52 in the direction of arrow D. Flared head 58 and accordingly cylinder 52 is then prevented from being moved away from handle 20 by nose 34. To detach the cylinder 52 from the handle 20, the locking lever 30 is again actuated to move the head 32 and nose 34 back away from the cylinder 52 to permit the flared end 58 of cylinder 52 to move past nose 34.

Importantly, the sampling end should couple and decouple with the handle with ease to allow for the sleeve to be readily interchangeable with the handle. It may be desirable to operate a probe in an automated environment wherein the handle is positioned to grab a sampling end, use the sampling end to take a measurement of a solution, release the end and grab another for another measurement. It is desirable that sampling ends with different size characteristics in terms of the gap A of the sample chamber are readily interchangeable with a given probe handle, so that one probe device can be used with different sampling ends for different applications.

Figure 6:
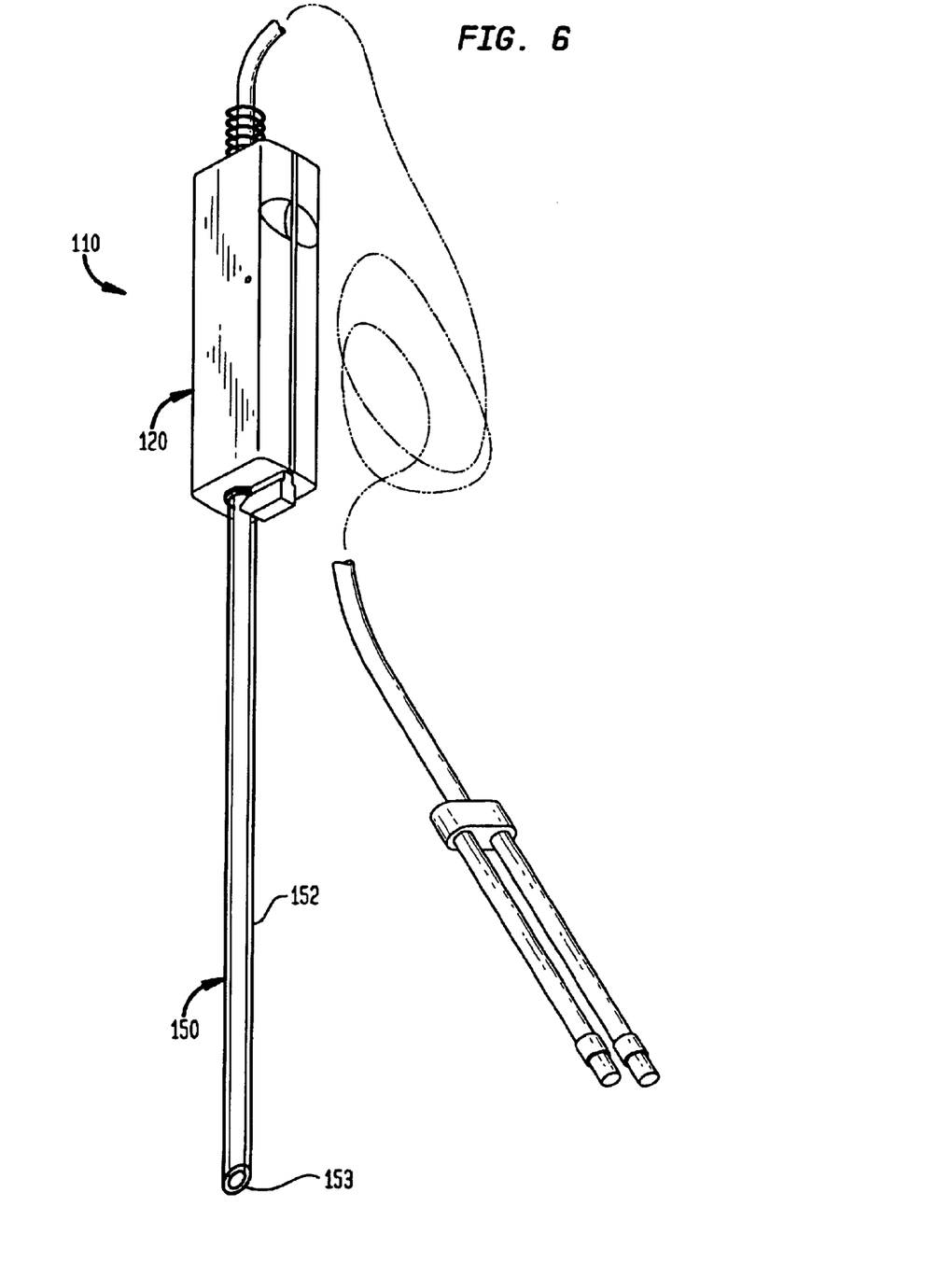
FIG. 6 is a perspective view of another embodiment of the fiber optic probe device of the present invention.

In another embodiment, as shown in FIG. 6, of the probe 110 of the present invention, the sampling end 150 can be used without a sample chamber and without a reflective surface. The sampling end 150 includes a cylinder 152 attachable to handle 120. Such a configuration is known as an Optrode or transducer. The outer side of the optical window 153 of the elongated tube 152 can be coated with a chemical composition which may be reactive with a component of a fluid medium. The chemicals may be deposited on the end and in contact with the solution being measured, or may be positioned under protective coatings and out of contact with the solution. Light from the fiber optics can pass back and forth through the optical window of the elongated tube. Any reaction caused by the chemical composition will influence the light returning to the fiber optics and provide data on the fluid medium.

The transducer can be absorption or fluorescence based. It could put light into a sample and measure changes therein, or it could be photoactivated, i.e. when the appropriate light pulse is provided to the solution, the material is "turned on." In another type of transducer, there is no input light but the material reacts in the presence of an analyte or with non-optical excitation, by emitting light. Such transducers detect bio-, chemi-, cathodo-, electron, and tribo-luminescence.

In any of the embodiments of the present invention, it is desirable that the sampling end comprises non-reactive components. Preferably, reactive organic adhesives are not used to interconnect the optical window to the elongated tube, nor to interconnect the channel with the elongated tube. Rather, the components are integrally formed, or are interconnected by non-reactive means such as fusing. In a preferred embodiment, the elongated tube and the channel are made of glass (silica) and are fused together. Other materials can be used including, but not limited to polytetrafluorethylen made by DuPont and sold under the brand name Teflon. This results in a generally non-reactive sampling end. Depending on the application, it may be acceptable for the sampling end to be made of any other desired material such as plastic, etc. Of course, a specific material will not be inert for all materials, or it may work for a period of time before failing, i.e. the sampling end could be semi-inert in a particular environment. The reflective coating on the bottom wall of the channel is preferably aluminum, but this can be varied. If a fluid medium to be analyzed contains components that are reactive with aluminum, it would be desirable to change to composition of the reflective coating.

Figure 9A:
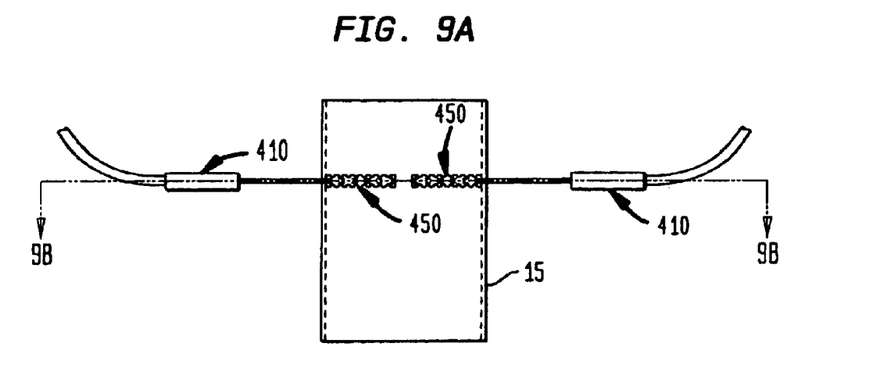
FIG. 9A shows a top view of an embodiment of the fiber optic probe device shown in FIG. 1 positioned across a pipe.
Figure 9B:
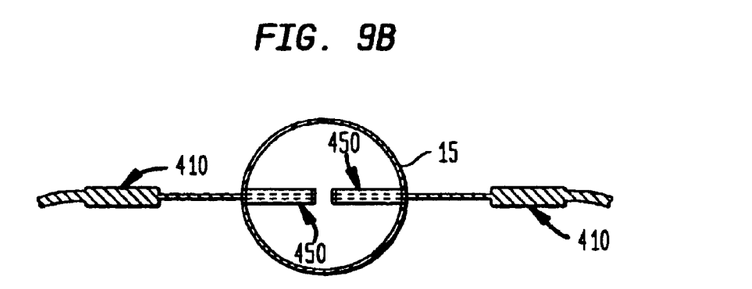
FIG. 9B is a cross-section thereof along the line 9B—9B in FIG. 9A.

The configuration of the sampling end of the present invention can be varied without departing from the scope of the present invention. For example, it could be desirable to make the entire sampling end into a rectangular shape, or even a round shape. It may be desirable to have multiple ends coming together, i.e. two ends that are 90 degrees apart and meet at or near their bottom ends. This type of configuration could be useful for certain measurement modalities such as fluorescence. In another application, two sampling ends could oppose each other in a facing relation. For example, as shown in FIGS. 9A and 9B two sampling ends 450 could oppose each other for taking measurements across a pipe 15. Two probes 410 can be used, one inserted in each of the two sampling ends 450 formed in pipe 15. One probe 410 can send light and the other probe 410 can receive it to test solutions flowing through a pipe. The optical fibers of probes 410 can be brought into contact with the distal ends of sample ends 450 to take measurements. Again, the angle between the probes could be varied in accordance with the application. The angle could be 180° as shown, 90°, 45°, etc.

It may be desirable for the end to be made of a flexible material, particularly, if measurements are being taken at long distances, for example, where the sensor is placed into a harsh environment. Depending upon the environment, it may be desirable to coat the outside of the sampling end and/or the side walls of the optical chamber, i.e. surfaces that are not optical surfaces. These coatings can be made out of various materials for protection of the sampling end in specific environments, for example, Teflon or some other medical grade plastics, or just to make end less susceptible to fractures. Another use of a coating is to reduce light contamination (stray light) into the probe, i.e. an anti-reflective coating to reduce noise. Indeed, it may be desirable to coat the entire sampling end in a black color to block light except at its distal end.

Modifications can be made to the sampling end of the present invention. For example, fibers could be incorporated into the cylinder for illumination or detection purposes. A fiber could be formed integrally within the sampling end or, the end could be fabricated entirely out of fibers or capillary tubing. Light could come from the handle and be sent along the walls of the sampling end for outputting light, and a single large core fiber at the center of the sampling end could receive reflected light. Fibers from different instruments could be bundled and positioned within a sampling end to allow for multi-instrument measurements.

In use, a sampling end is placed over optical fibers extending from a handle. The sampling end is attached to the handle or to the optical fibers. Alternatively, the sampling end could be fixed at a predetermined location and the optical fibers inserted thereinto. Preferably, the optical fibers contact the inner surface of the distal end of the sampling end and are biased thereagainst. The probe can then be placed into a solution and measurements can be taken. Thereafter, the probe can be removed from the solution and the sampling end disengaged. The sampling end can then be discarded, and a new sampling end attached to the probe. Alternatively, the used sampling end can be cleaned, sterilized if necessary, and reused. Such cleaning and sterilization could be conducted with the sampling end attached to or detached from the probe.

Figure 10A:
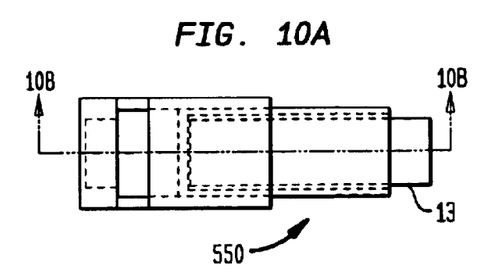
FIGS. 10A–10D shown another embodiment of the fiber optic probe device of the present invention.
Figure 10B:
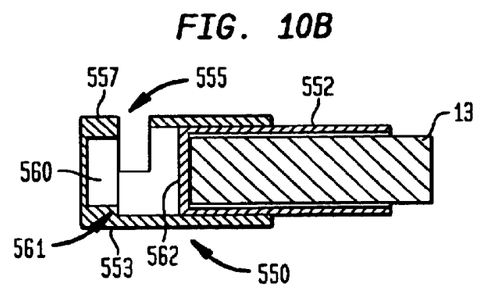
Figure 10C:
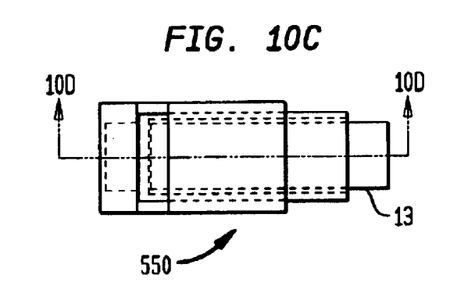
Figure 10D:
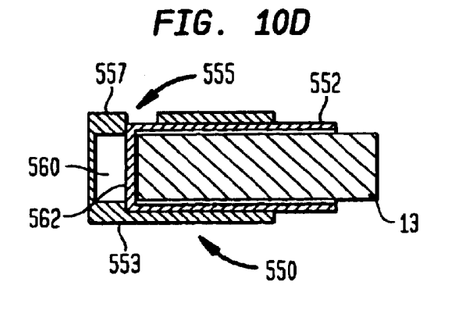

FIG. 10A is a top view of another embodiment of a sampling end, generally indicated at 550 of the present invention. FIG. 10B is a cross-sectional view of the device shown in FIG. 10A taken along the line 10B—10B. FIG. 10C is a view of the sampling end shown in FIG. 10A in a retracted position and FIG. 10D is a cross-section view of the sampling end shown in FIG. 10C taken along the line 10D—10D.

The sampling end 550 shown in FIGS. 10A–10D interconnects directly with an optical fiber or fibers 13. This type of connection could be used with all embodiments of the present invention. The interconnection between optical fiber or fibers 13 and sampling end 550 can be based on a friction fit between the optical fiber or fibers and the sampling end. In another configuration, the interface of the distal end of fiber or fibers 13 against the closed end 562 can create a stiction which couples the sampling end 550 with the optical fiber or fibers 13. Optical grease could be used to enhance stiction. It is also within the scope of the invention to provide a means for enhancing the frictional fit of sampling end 550 and fiber or fibers 13 such as the provision of a flexible member having a high coefficient of friction at the proximal end of the sampling end or the provision of a washer or another construct within the cylindrical member 552 that frictionally engages the fiber or fibers.

As also shown in FIGS. 10A–10D, an articulated sample tip can be formed by second cylindrical member 553 and which rides first cylindrical member 552 and can be telescoped out and back from the first cylindrical member 552. The second cylindrical member 553 includes an end cap 557 having a cylindrical portion and an end wall, and a slot 555. The second cylindrical member 553 can be adjusted away from or against first cylindrical member 552. A solution to be sampled can flow into the sample chamber 560 through slot 555. Second cylindrical member 553 can be closed against first cylindrical member 552 to close slot 555 and retain solution in sample chamber 560, allowing the sample to be withdrawn for subsequent testing or storage. A step 561 on the interior of the second cylindrical member 553 coacts with the first cylindrical member 552 to provide accurate gap control.

Figure 11A:
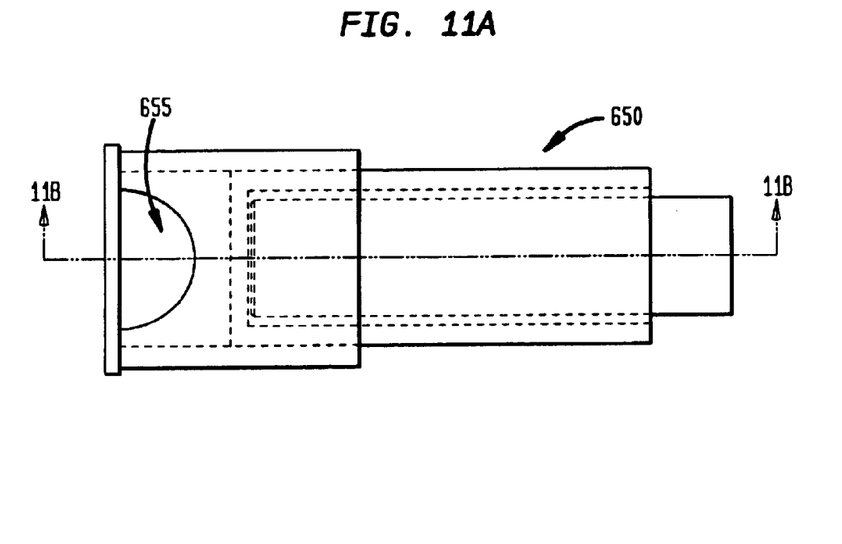
FIG. 11A is a top view of another embodiment of the fiber optic probe device of the present invention.
Figure 11B:
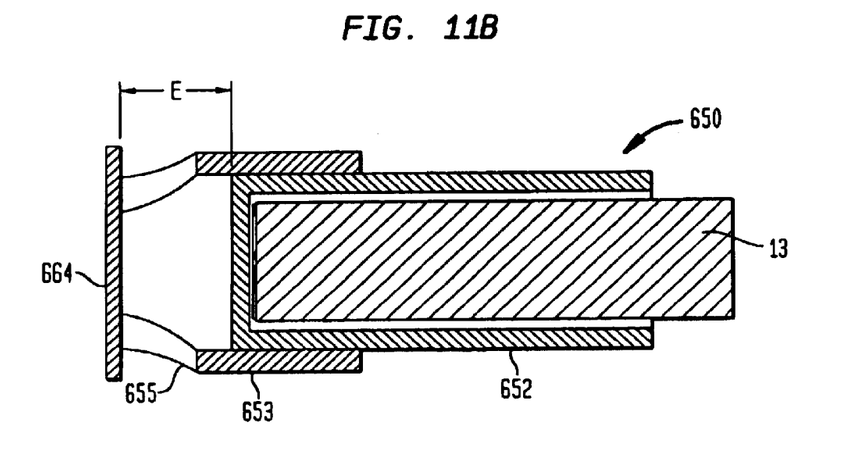
FIG. 11B is a cross-sectional view of the device shown in FIG. 11A taken along lines 11B—11B.

FIG. 11A is a top view of another embodiment of the fiber optic probe device of the present invention, and FIG. 11B is a cross-sectional view of the device shown in FIG. 11A taken along lines 11B—11B. A sampling end 650 is provided for an optical fiber or fibers 13 including a first cylindrical member 652 and a second cylindrical member 653. The second cylindrical member 653 can telescope with respect to the first cylinder 652. Mechanical means may be employed to accurately gage and determine gap E. Openings 655 are provided between the outer cylindrical wall 653 and end wall 664 which carries a mirror.

Figure 12:
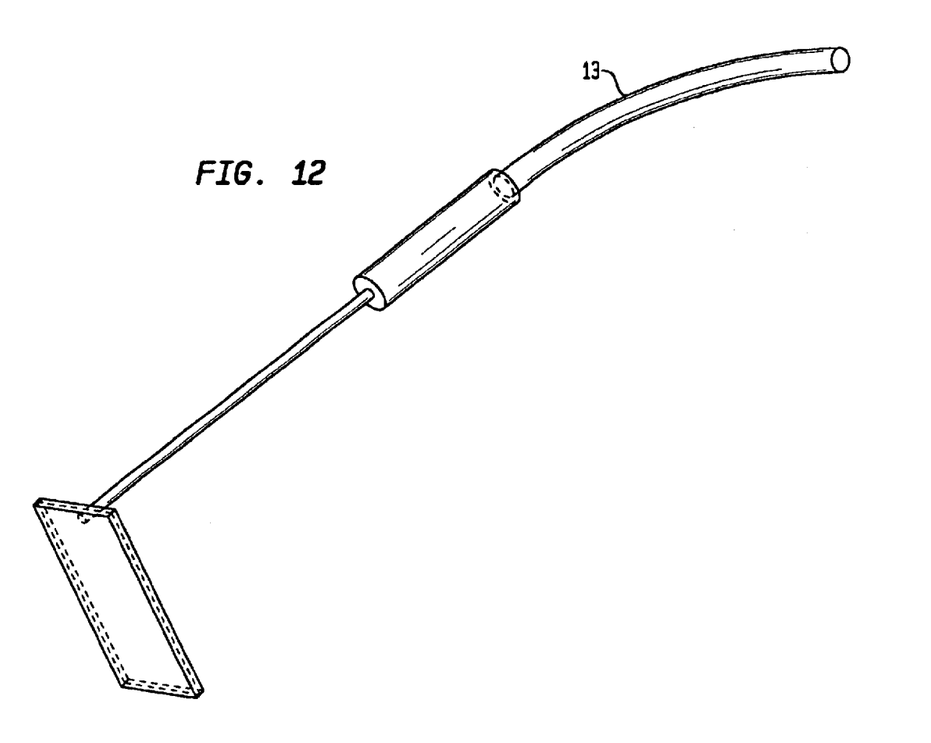
FIG. 12 shows another embodiment of the fiber optical probe device of the present invention.

FIG. 12A shows another embodiment of the fiber optical probe device of the present invention wherein an optical fiber 13 can be held against a capillary 760 of any cross section. Such a capillary could merely be two spaced apart sheets, e.g. slides, that wick solution therebetween. The optical fiber can be positioned within a sampling end 750 or can be used without a sampling end. Coatings, electrodes and transducers are similar to those described herein. FIG. 12B shows another embodiment wherein a capillary 762 extends from the closed end of sampling end 750. Capillary 762 wicks solution to be tested into an area proximate the optical window. Reactants can be included within the capillary for interacting with the sample.

Figure 13A:
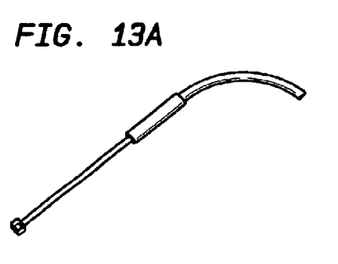
FIGS. 13A and 13B show a chamber wherein the sample end can be held against the sample chamber.
Figure 13B:
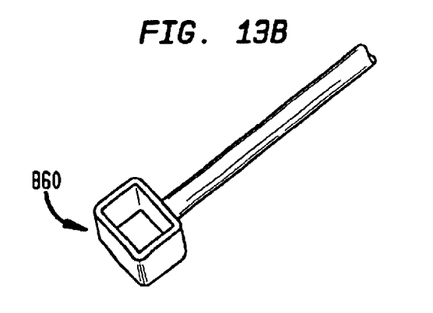

FIGS. 13A and 13B similarly show a chamber 860 wherein the sampling end 850 containing one or more optical fibers 13, or the fibers themselves, or a sampling end according to the present invention, or any other known fiber optic probe device, can be held against the sample chamber by various means. After use, the sampling end can be cleaned, the sample chamber discarded, and a new sample chamber can be used. It should also be pointed out that the sample chamber could be releasably interconnected with the sampling end such as by a mechanical clip. Indeed, sample chambers of various sizes can be used with a sampling end. This would allow the pathlength to be adjusted in a very precise manner—more precisely than a configuration where the reflective surface is moveable with respect to the optical window.

Figure 14:
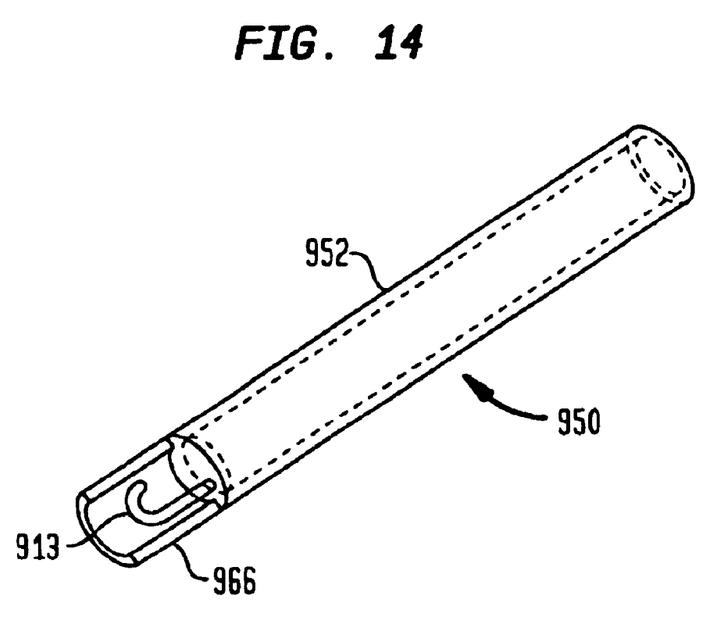
FIG. 14 is another embodiment of the sampling end of the present invention wherein the sampling end utilizes a fiber instead of a mirror to direct light from one optical fiber to another.

FIG. 14 is another embodiment of the sampling end 950 of the present invention that utilized a return fiber 913 instead of a mirror to direct light from the "outside" of the probe to the "inside." The return fiber 913 is mounted on the closed end 963 of the sampling end and extends a distance and curves to face back to the closed end. The distance from the face of the return fiber 913 to the optical window on the closed end of the sampling end defines the pathlength. Alternatively, a prism could be used instead of return fiber 913. As illustrated, a protective skirt 966 can be used to partially or fully surround the return fiber 913 or prism for protection.

There could also be additional variations to the sampling end of the present invention. For example, the sampling end could be made of a capsule material that dissolves over time. A very short pathlength probe could make use of capillary action to draw a sample into a measurement area. The sample could be capped and saved/archived for later measurement/analysis. Additional instrumentation could be integrated into the sampling end for measuring PH, delivering an electrical charge, etc. Optical fibers could be buried in the sampling end to create a ring of light on top. In some instances the sampling end could be keyed to interconnect at a desired orientation with a handle. A stand or holder could be used to support multiple sampling ends in position where they can be grabbed and used. Such a stand would be particularly useful in an automated setting.

Having thus described the invention in detail, it is to be understood that the foregoing description is not intended to limit the spirit and scope thereof. What is desired to be protected by Letters Patent is set forth in the appended claims.

What is claimed is:

1. A fiber optic probe apparatus comprising:
   an analyzer;
   a handle;
   one or more optical fibers extending from the analyzer and the handle;
   a sampling end positionable over the one or more optical fibers, the sampling end including an open end for receiving the one or more optical fibers and a closed end, the closed end including an optical window; and
   means at the proximal end of the sampling end for releasable attachment to the handle.

2. The apparatus of claim 1 wherein the sampling end further comprises a sample chamber at the closed end.

3. The apparatus of claim 2 wherein the sample chamber comprises a reflective surface in facing relation to the optical window.

4. The apparatus of claim 3 wherein the reflective surface is maintained in facing relation to the optical window by one or more support members.

5. The apparatus of claim 4 further comprising a membrane filter which physically or chemically filters the sample entering the sample chamber.

6. The apparatus of claim 5 wherein the reflective surface is moveable with respect to the closed end of the sampling end to vary the pathlength of the sample chamber.

7. The apparatus of claim 6 wherein the support members telescope along the distal end of the sampling end to vary the position of the reflective surface with respect to the closed end of the sampling end.

8. The apparatus of claim 7 wherein a storage chamber is formed in the space between the reflective surface and to the closed end of the sampling end when the reflective surface is retracted.

9. The apparatus of claim 3 wherein the reflective surface comprises a reflective coating on a substrate.

10. The apparatus of claim 9 wherein the reflective coating comprises aluminum.

11. The apparatus of claim 9 wherein the reflective coating comprises gold.

12. The apparatus of claim 4 wherein the support members include slots for receiving the reflective surface.

13. The apparatus of claim 12 wherein the reflective surface is fixed within the slots.

14. The apparatus of claim 2 further comprising a sensor at the distal end of the sample chamber.

15. The apparatus of claim 14 further comprising an electrical lead connecting the sensor to the analyzer.

16. The apparatus of claim 15 wherein the electrical lead is embedded in the sampling end along the length of the sampling end.

17. The apparatus of claim 16 further comprising means for orienting the sampling end with respect to the handle for electrically communicating the electrical lead and the handle.

18. The apparatus of claim 15 wherein the electrical lead extends within a capillary tube attached to the sampling end.

19. The apparatus of claim 15 wherein the electrical lead extends from the sampling end to the handle and then to the analyzer.

20. The apparatus of claim 2 wherein the sample chamber is formed of a unitary construction with the sampling end.

21. The apparatus of claim 2 further comprising a filter applied to the optical window.

22. The apparatus of claim 2 wherein the sample chamber is fused to the sampling end.

23. The apparatus of claim 1 wherein the sampling end is placed into contact with a surface for taking a sample.

24. The apparatus of claim 23 wherein the surface comprises a sample chamber.

25. The apparatus of claim 24 wherein the sampling end is attachable to the sample chamber.

26. The apparatus of claim 25 wherein one or more clips attach the sampling end to the sample chamber.

27. The apparatus of claim 23 wherein the surface comprises a capillary sample holder.

28. The apparatus of claim 1 wherein the sampling end is incorporated in a vessel and the one or more optical fibers are inserted therein.

29. The apparatus of claim 28 where in the sampling end is incorporated into a pipe.

30. The apparatus of claim 28 wherein two sampling ends are incorporated into a pipe in facing relation.

31. The apparatus of claim 28 wherein two sampling ends are incorporated into a pipe with an angle formed between the sampling ends.

32. The apparatus of claim 1 wherein a return fiber extends from the closed end of the sampling end in U-shape to face back to the closed end of the sampling end.

33. The apparatus of claim 32 wherein two optical fibers are inserted into the sampling end, one aligning with the return fiber extending from the closed end and the other aligning with the end of the return fiber facing back to the closed end.

34. The apparatus of claim 32 wherein the device includes an orientation means for orienting the sampling end with the optical fibers to align the optical fibers with the return fiber.

35. The apparatus of claim 32 wherein a shield is positioned about the return fiber to provide protection.

36. The apparatus of claim 1 further comprising a capillary extending from the closed end.

37. A The apparatus of claim 36 wherein a reactant is included within the capillary.

38. The apparatus of claim 1 further comprising a chemical composition on the exterior of the optical window for chemical interaction with a solution under test.

39. The apparatus of claim 1 wherein distal ends of the one or more optical fibers bear against the closed end of the sleeve.

40. The apparatus of claim 1 wherein the sampling end is attachable to the one or more optical fibers.

41. The apparatus of claim 1 wherein one or more optical fibers extending from the handle are moveable with respect to the handle and the one or more optical fibers contact the closed end of the sampling end and are biased thereagainst when the sampling end is interconnected with the handle.

42. The apparatus of claim 1 wherein the means at the proximal end of the sampling end includes a ridge and the handle includes a moveable lever that coacts with the ridge to releasbly attach the sampling end to the handle.

43. The apparatus of claim 1 wherein the optical window is formed integrally with the sampling end.

44. The apparatus of claim 1 wherein the optical window is fused to the sampling end.

45. The apparatus of claim 1 further comprising a filter applied to the optical window.

46. The apparatus of claim 1 further comprising an optical component at the closed end.

47. A fiber optic probe apparatus comprising:
a handle;
optical fibers extending from the handle;
a sampling end positionable over the optical fibers and releasably attached to the handle;
a sample chamber at the distal end of the sampling end, the sample chamber including:
upper and lower walls in facing relation;
side walls extending between the upper and lower walls to form a chamber having open ends; and
a reflective coating on the lower wall.

48. The apparatus of claim 47 wherein the upper wall of the sample chamber comprises an optical window.

49. The apparatus of claim 48 further comprising a filter applied to the upper wall of the sample chamber.

50. The apparatus of claim 48 further comprising a membrane filter over the sample chamber.

51. The apparatus of claim 47 wherein the sample chamber is fused to the sampling end.

52. The apparatus of claim 47 wherein the sampling end and sampling chamber is of a unitary construction.

53. A fiber optic probe apparatus comprising:
an analyzer;
a handle;
one or more optical fibers extending from the analyzer and the handle; and
a sampling end with a sampling chamber for holding a sample of a solution to be test, the sampling end releasably attachable to the handle.

54. The apparatus of claim 53 wherein the optical fibers are positioned against the sample chamber.

55. The apparatus of claim 54 wherein the sample chamber comprises a capillary apparatus.

56. The apparatus of claim 53 wherein the sampling chamber is releasably attached to the sampling end.

57. The apparatus of claim 56 wherein the sampling chamber is releasably attached to the sampling chamber by clips.

58. The apparatus of claim 53 wherein the sample chamber comprises an optical window at one surface and a reflective surface in an opposing relation.

59. A method of using a fiber optic probe to sample a solution comprising:
providing a fiber optic probe handle with optical fibers extending therefrom;
providing an attachment mechanism on the handle for releasably attaching and detaching a sleeve to the handle;
providing a sleeve having an open upper end and a closed lower end;
attaching the sleeve to the handle, the sleeve covering a distal portion of the optical fibers;
sampling a solution by inserting the sleeve into a solution; and
removing the sleeve from the solution.

60. The method of claim 59 comprising releasing the sleeve from the handle and discarding the sleeve.

61. The method of claim 60 further comprising the step of attaching another sleeve to the handle for additional sampling.

62. The method of claim 61 wherein a plurality of sleeves are arranged on a holder and sleeves can be automatically attached and released from the handle without the need for human intervention.

63. The method of claim 59 further comprising releasing the sleeve from the handle, cleaning the sleeve and reattaching the sleeve to the handle.

64. The method of claim 63 further comprising sterilizing the sleeve.

65. The method of claim 59 further comprising cleaning the sleeve and using the sleeve for additional sampling.

66. A fiber optic probe apparatus comprising:
an analyzer:
one or more optical fibers extending from the analyzer;
a sampling end positionable over the one or more optical fibers, the sampling end including an open end for receiving the one or more optical fibers and a closed end, the closed end including an optical window;
a sample chamber at the closed end of the sampling end;
a sensor at the distal end of the sampling chamber; and
an electrical lead connecting the sensor to the analyzer.

67. The apparatus of claim 66 wherein the electrical lead is embedded in the sampling end along the length of the sampling end.

68. The apparatus of claim 66 wherein the electrical lead extends within a capillary tube attached to the sampling end.

69. The apparatus of claim 66 wherein the sampling end connects to a handle and the electrical lead extends from the sampling end to the handle and then to the processor.

70. The apparatus of claim 66 further comprising means for orienting the sampling end with respect to the handle for electrically communicating the electrical lead and the handle.

71. A sampling end for a fiber optic probe comprising:
a closed end having an optical window;
a sample chamber at the closed end;
an open end for receiving one or more fibers of a fiber optic probe; and
means for releasably attaching the sampling end to a fiber optic probe handle.

72. The apparatus of claim 71 wherein the sample chamber comprises a reflective surface in facing relation to the optical window.

73. The apparatus of claim 72 wherein the reflective surface is maintained in facing relation to the optical window by one or more support members.

74. The apparatus of claim 72 wherein the reflective surface comprises a reflective coating on a substrate.

75. The sampling end of claim 71 wherein the means at the proximal end of the sampling end includes a ridge and the handle includes a moveable lever that coacts with the ridge to releasbly attach the sampling end to the handle.

76. The apparatus of claim 71 wherein the optical window is formed integrally with the sampling end.

77. The apparatus of claim 71 wherein the optical window is fused to the sampling end.

78. The apparatus of claim 71 wherein the sample chamber is formed of a unitary construction with the sampling end.

79. The apparatus of claim 71 wherein the sample chamber is fused to the sampling end.

* * * * *